(12) United States Patent
Bernard et al.

(10) Patent No.: US 11,241,554 B2
(45) Date of Patent: Feb. 8, 2022

(54) MANUFACTURING METHOD FOR A HOOD TYPE VENTILATION DEVICE

(71) Applicants: Edward Helmut Bernard, Maidstone (CA); Will James Cipkar, Amherstburg (CA); William Cipkar, Amherstburg (CA); Brian Gignac, LaSalle (CA)

(72) Inventors: Edward Helmut Bernard, Maidstone (CA); Will James Cipkar, Amherstburg (CA); William Cipkar, Amherstburg (CA); Brian Gignac, LaSalle (CA)

(73) Assignee: CREST MOLD TECHNOLOGY INC., Oldcastle (CA)

( * ) Notice: Subject to any disclaimer, the term of this patent is extended or adjusted under 35 U.S.C. 154(b) by 0 days.

(21) Appl. No.: 17/323,030

(22) Filed: May 18, 2021

(65) Prior Publication Data

US 2021/0379312 A1 Dec. 9, 2021

Related U.S. Application Data

(60) Provisional application No. 63/035,236, filed on Jun. 5, 2020.

(51) Int. Cl.
*A61M 16/06* (2006.01)
*B29C 45/16* (2006.01)
*B29L 31/00* (2006.01)
*B29L 31/48* (2006.01)

(52) U.S. Cl.
CPC ..... *A61M 16/0627* (2014.02); *B29C 45/1676* (2013.01); *A61M 2207/00* (2013.01); *B29L 2031/4835* (2013.01); *B29L 2031/753* (2013.01)

(58) Field of Classification Search
CPC ....... A62B 17/04; A62B 19/04; A62B 18/045; A62B 18/084; A41D 13/1153; A41D 13/1218; A41D 2200/20; A42B 1/048; A42B 1/205; A42B 7/00; A61M 16/0627; B63B 11/06; B64D 10/00; B64D 2010/002–005
See application file for complete search history.

(56) References Cited

U.S. PATENT DOCUMENTS

| | | | | |
|---|---|---|---|---|
| 5,819,728 | A * | 10/1998 | Ritchie | A62B 17/04 128/201.23 |
| 6,854,459 | B1 * | 2/2005 | Cox | A62B 17/04 128/201.22 |
| 8,613,113 | B1 * | 12/2013 | Resnick | A62B 17/04 2/410 |
| 2006/0137686 | A1 * | 6/2006 | Macris | A61M 16/06 128/201.22 |
| 2011/0226240 | A1 * | 9/2011 | Navalesi | A61M 16/06 128/201.23 |

(Continued)

*Primary Examiner* — Valerie L Woodward

(57) ABSTRACT

A device for providing a known concentration of blended air and oxygen, or oxygen, to an individual which incorporates a face mask inside a hood, thereby preventing aerosolization of potentially harmful exhaled gases and controlling condensation issues within the hood while under pressurized conditions. The air tight seal required to allow placement and removal of the hood on the individual will be manufactured using injection molded elastomers to over-mold injection molded rigid plastic components.

7 Claims, 13 Drawing Sheets

(56) References Cited

U.S. PATENT DOCUMENTS

| | | | | |
|---|---|---|---|---|
| 2014/0331999 A1* | 11/2014 | Rossi | ................ | A61M 16/0627 |
| | | | | 128/202.27 |
| 2015/0297854 A1* | 10/2015 | McCracken | ...... | A61M 16/0825 |
| | | | | 128/201.23 |
| 2020/0206544 A1* | 7/2020 | Vaughan | ................ | A62B 17/04 |

* cited by examiner

Cross Section View

MANUFACTURING METHOD FOR A HOOD TYPE VENTILATION DEVICE

BACKGROUND OF THE INVENTION

The invention pertains to non-invasive ventilation. CPAP or Continuous Positive Airway Pressure is a well-known treatment modality (also known as NIV or non-invasive ventilation) that has been in use for many years. Air flow is introduced into the airways at a higher atmospheric pressure to assist the patient's own breathing efforts by preventing airway collapse and "stenting" the airway open. This is used by patients who are conscious and able to breathe spontaneously and allows for less work of breathing and improved airway function. PEEP (Positive End Expiratory Pressure) is the amount of pressure remaining in the alveoli at the end of expiration above that of atmospheric pressure. CPAP is one method of delivering PEEP, which in turn increases the surface area of the alveoli available for oxygen exchange, decreases atelectasis and improves ventilation/perfusion matching. As a result, oxygenation is improved.

The present invention relates to a helmet for providing assisted respiration and non-invasive ventilation without the aid of a standard CPAP facial mask, BiPAP (Bi-level Positive Airway Pressure) facial mask or endotracheal tube. In oxygenation and ventilation with continuous positive pressure, several different modalities are currently used including helmets, this latter entity comprising a container body made of a flexible plastic material and equipped with a collar for air-tight application to the patient's head. In the known helmets, the flexible container body is equipped with an air inlet mouth connected to a ventilation machine and a discharge outlet.

SUMMARY OF THE INVENTION

The invention pertains to a helmet or hood NIV apparatus including a soft malleable plasticized container that attaches to a solid neck ring with an elasticized seal. The connection between the neck ring and hood has been adapted to facilitate a closed leak-proof container that is simple and easy to remove. In prior art, the hood portion can be connected to the neck ring via several means to generate the clamping pressure required to produce an air-tight seal on a compressible O-Ring (that will be molded in place rather than having to be "installed"), between the two items. This invention produces two air-tight seals without the use of O-rings by over-molding elastomer materials onto rigid plastic substrate geometries, using chemical bonding as well as a flow through concept where the rigid part geometry has been designed to provide flow channels in a secondary position (within the mold) to allow the secondary injection of the elastomer materials, to deliver these molten materials into the secondary geometry of the mold where the elastomer material of the neck seal can also flow through the inner neck ring of the dashboard/console to also produce a pre-loaded protrusion of the elastomer, to function similarly to an O-Ring but (unlike an O-ring seal) will not be subject to improper positioning because it will be molded in place and chemically bonded into position, with the attached physical restraint provided by the contiguous cured elastomer material which connects, seals, and bonds (in position) these three (according to prior art the neck collar has to be manually stretched and assembled onto an inner neck ring after manually assembling an O-ring into a groove around the periphery) different components are permanently assembled within the mold during the single molding cycle.

In application, this three-piece construction (produced in a single molding cycle of less than 2 minutes total) is pulled over the patient's head so that the neck collar produces an air-tight fit to the patient's neck. Once the associated medical support apparatus has been attached to the dashboard/console of the inner neck ring (like oxygen tubes, entertainment connections, anti-asphyxiation, PEEP valves, etc.) and the patient is comfortable, a face mask with a (just long enough) flexible air tube is fitted to the patient's face and connected to the inner neck ring console, before the second part of the invention can be installed over the patient's head and be made to also create an air-tight seal between the (already positioned on the patient) inner neck ring and the outer neck ring, which is also over-molded with the transparent and soft hood. The air pressures in the face mask, and the atmospheric pressure within the hood will be different, and dynamic in the relationship to each other, as well as their relationship to room atmosphere pressure, and the novelty of this combined pressure effect provides medical advantages to the patient by preventing alveoli from complete deflation, making it easier for the patient to breathe using the power of their own diaphragm muscles, without having to be clinically paralyzed, intubated, and placed on life support. The invention provides the double use of either the elastomer material of the neck collar on the inner neck ring (where it becomes another sealing surface between the outer periphery of the inner neck ring and the inner periphery of the outer neck ring), and/or the double use of the other elastomer material being double-shot over the rigid outer neck ring where the over-molded elastomer hood material is made to flow into a channel geometry on the outer neck ring also intended to produce a protruding surface capable of creating an air-tight seal (replacing the need to install and suppress an O-ring, which can roll out of position while attempting to create an air-tight seal with mating components). The possible methods to hold the over-molded elastomer seal surface against the mating hard (first shot) can include, a bayonet style engagement, screws, clamps, cam locks, etc. These can all be categorized as manually operated locking mechanisms. The method described herein is a cam lock style mechanism.

The double seal "push/pull" (double safe) concept, with the pie-shaped (unsupported) flap (around the periphery of the inner diameter of the outer neck ring) of soft hood plastic becomes supported once the rigid outer neck ring (with the hood over-molded) is fitted against the (increasing load) interference ribs on the inner neck ring of the over-molded neck collar so that after the two are clamped together in this sealed (tapered) fit relationship between the outer neck ring sandwiching the soft hood plastic with the inner neck ring, this pie-shaped (now supported by the mating inner neck ring's rigid material) becomes increasingly sealed against the inner neck ring after the hood becomes pressurized during therapeutic use.

It is also possible that the residual pressurized air can be distributed through an independent circuit of molded-in channels to provide air flow beneath the rubber neck collar of the inner neck ring.

This process design has been conceived to reduce individual product costs through innovative tooling and automation so that the production costs are low enough to introduce this product as "disposable" (and fully recyclable) after use on a patient.

The aforementioned features will be integral 'as molded', based on features and capabilities conceptualized by physicians to provide postponement of intubation, have been (in the subject of this disclosure) designed for manufacturability optimization, using new in-mold assembly, quality assured, lowest manufacturing cost, and novel multiple material finished assemblies produced every cycle of molding process operation. The invention has several improvements to previous helmet designs that are novel and will be detailed in this disclosure.

Specifically, there is a novel combination of medical methods that requires new apparatus to be designed and fabricated, using injection molding technologies combined with rubber seal conditions and a balance between two different atmospheric pressure-controlled environments. This product has been designed for COVID-19 treatment but has other applications as well.

Oxygen tubing and air tubing is connected to the standard hospital wall outlets. These tubes can then be attached together via an air/oxygen supply "Y" adaptor or a commercially available oxygen blender. This single blended air/oxygen tube then attaches to an anti-asphyxiation valve before attaching to the intake port on the underside of the neck ring.

Oxygen tubing is then attached from the interior of the neck ring to a customized face mask which is then affixed to the patient's face. The face mask employs both intake and outflow backflow preventers ensuring accurate oxygen/air concentrations. Additionally, the incorporation of the internal face mask, with its one-way air flow design eliminates the condensation build up within the hood which plagues currently available systems.

A length of corrugated oxygen tubing is attached to the exhalation port on the under surface of the neck ring. This is connected to an inline viral filter and finally to an adjustable PEEP valve.

There are additional ports in the neck ring and include the following items. There is a safety pressure relief valve, attached to a viral filter. There is an entertainment port for the ability to utilize earphones for entertainment or communication while wearing the hood. There is an additional port to permit access of a feeding tube or nasogastric tube should the patient's condition require one of these interventions.

An elasticized neck collar is attached to the upper surface of the inner neck ring. This can be cut to fit the patient's neck prior to use based on a sizing guide. The neck ring with attached elasticized seal is placed over the patient's head after the above-mentioned tubing has been attached. The face mask is placed on the patient's face with the desired blended air/oxygen mixture flowing. The hood is then placed over the patient's head and affixed to the inner neck ring. The air/oxygen mixture inflates the hood and the desired amount of pressure is set utilizing the PEEP valve. Retainer straps are affixed to the attachment sites on the neck ring and are employed to keep the neck ring/hood assembly from riding up and compromising the neck seal.

The neck ring includes a 'dashboard' of ports that can be customized and utilized for different functions based on specific patient needs, such as non-invasive ventilation in multiple environments including the emergency department, the intensive care unit, or the multi-place hyperbaric chamber.

The hood type ventilation device is a revolutionary non-invasive ventilation device that builds on long standing, proven effectiveness of helmet ventilation employed in Europe. The hood type ventilation device provides blended air and oxygen under positive pressure in a contained environment (known as a hood or helmet) to assist respiratory function and eliminate the risk of aerosolization of infective particles. The internal mask solves temperature and humidity issues of previous systems, as well as ensures the delivery of an accurately known and adjustable oxygen concentration (via an air/oxygen supply "Y" adaptor or a commercially available oxygen blender). The integral mask further benefits the hood's use by preventing the build-up of $CO_2$ surrounding the patient's breathing orifices. The design of the invention allows for aerosolized medications to be introduced into the closed circuit through the intake oxygen tubing and then delivered to the patient via the internal face mask.

This adaptation expands the treatment options for patients with underlying respiratory disease. The non-mechanized inflation system also obviates the need for dedicated pressure generating devices (such as CPAP or BiPAP machines), as it is pressurized solely by standard hospital oxygen/air sources. Safety is of paramount importance and the hood type ventilation device provides for redundancy factors ensuring both patient and caregiver protection. Patient safety enhancements include a pressure relief valve to ensure supra-therapeutic pressures are safely mitigated. Additionally, a protective anti-asphyxiation valve affixed to the entrainment limb ensures an adequate breathing supply should the hospital's oxygen/air delivery system or pre-patient components of the breathing apparatus fail. Caregiver protection includes viral filters on both the exhalation limb and the pressure relief safety system.

Patient comfort factors of the hood type ventilation device include ports for feeding/nutrition tubes for those who have swallowing difficulties or require around-the-clock hood usage. An entertainment port allows for headphone/microphone incorporation to provide both entertainment as well as enhanced communication ability with loved ones and the care team.

The novel manufacturing process enabling both the (in-mold assembled) three piece inner neck ring and the (in-mold assembled) three piece outer neck ring to have both internal and external over-molded elastomers that manage varying air pressures for oxygen therapy related functions using over-molded seals that are both chemically and mechanically bonded in their individual three piece assemblies, and are also mechanically sealed between the two, three piece assemblies when they are fastened together in their intended use. The clamps which will hold the inner neck ring (with the attached patient neck collar) and the outer neck ring (with attached hood) will also be integral to either of these two assemblies, so that they cannot be misplaced. By adding these four cam lock clamps to either of the three-piece (in-mold assembled) components, they become a seven-component assembly, that is entirely repeatable in a production environment, with quality control measures unaffected by human assembly anomalies.

BRIEF DESCRIPTION OF THE DRAWINGS

These and other objects of the invention will become apparent from reading a detailed description taken in conjunction with the drawings, in which.

DETAILED DESCRIPTION

Figure 1:
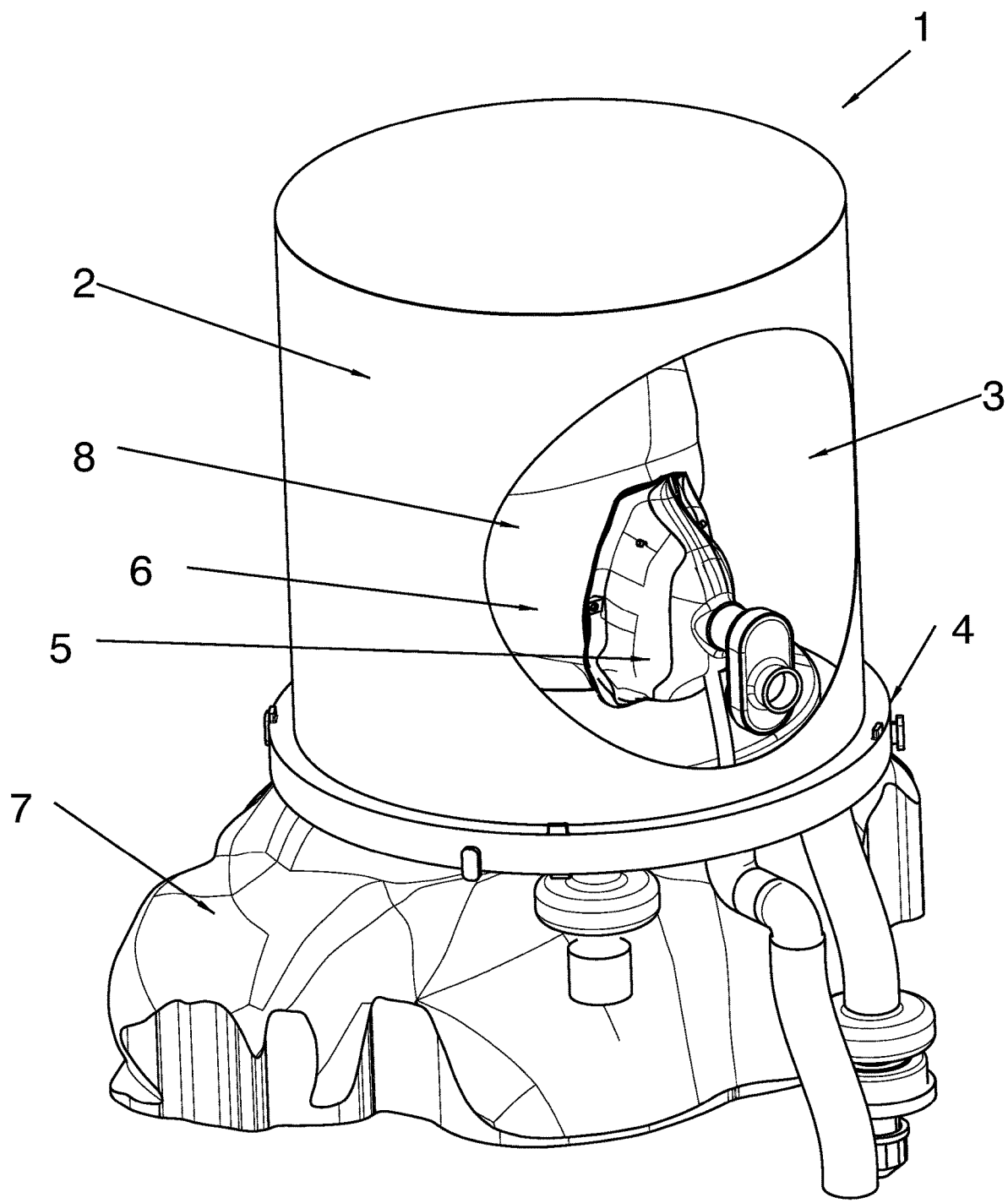
FIG. 1 is a drawing showing the non-invasive ventilation device being worn by a patient.

With reference to FIG. 1 the non-invasive ventilation device, 1, is shown. The major component pieces are: the hood, 2, the transparent view port, 3, the outer neck ring, 4, the face mask, 5, the patient's head, 6, the patient, 7, and the patient's face, 8. When installing the non-invasive ventilation device, 1, on the patient, 7, the inner neck ring, 9, is first lowered over the patient's head, 6, then the face mask, 5, is placed on the patient's face, 8, (making certain that the oxygen or air/oxygen mixture is turned on) and then the hood, 2, is placed over the patient's head, 6, and locked into place.

Figure 2:
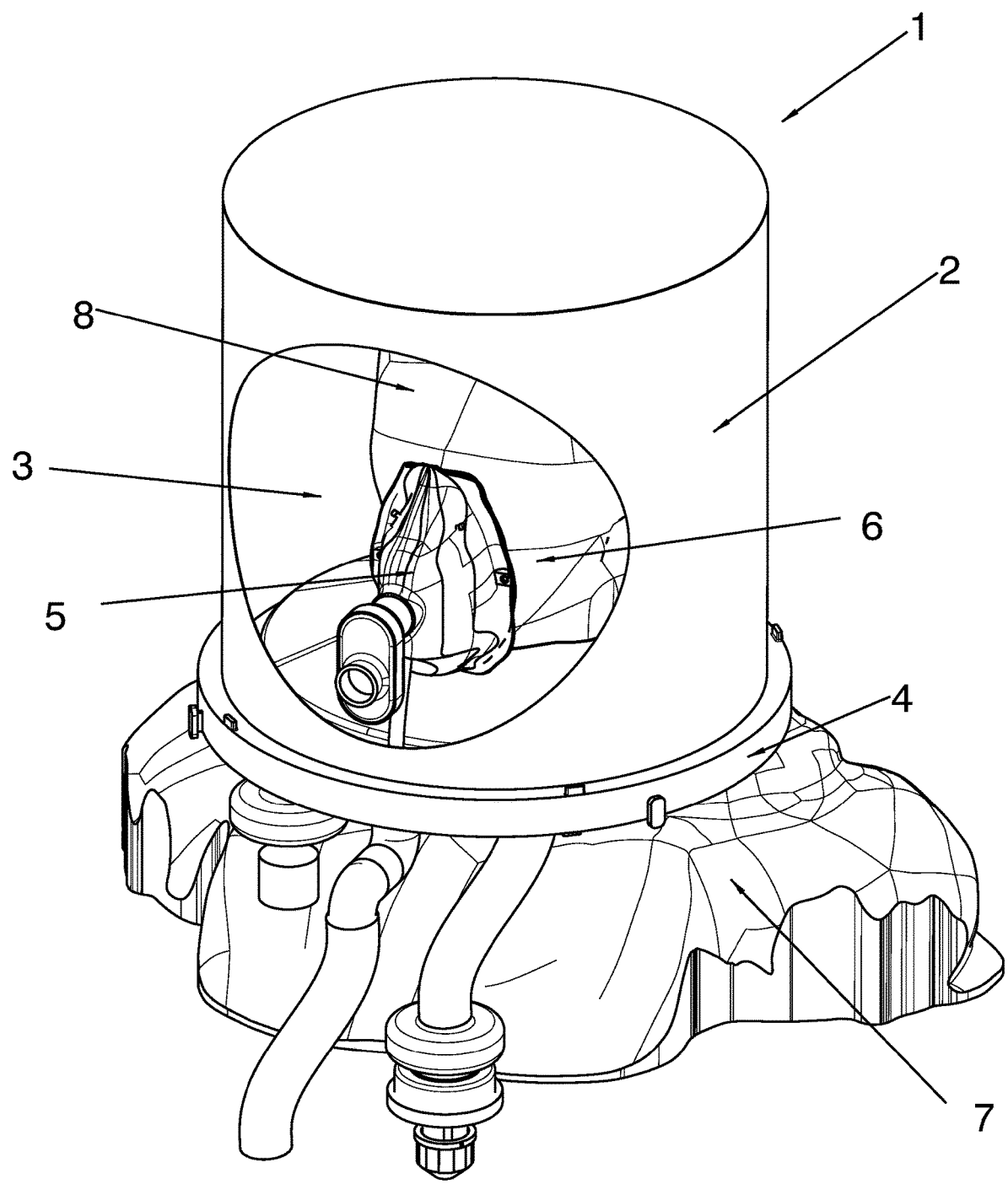
FIG. 2 is a drawing showing a second view of the non-invasive ventilation device being worn by a patient.

With reference to FIG. 2 a second view of the non-invasive ventilation device, 1, is shown. The major component pieces are: the hood, 2, the transparent view port, 3, the outer neck ring, 4, the face mask, 5, the patient's head, 6, the patient, 7, and the patient's face, 8.

Figure 3:
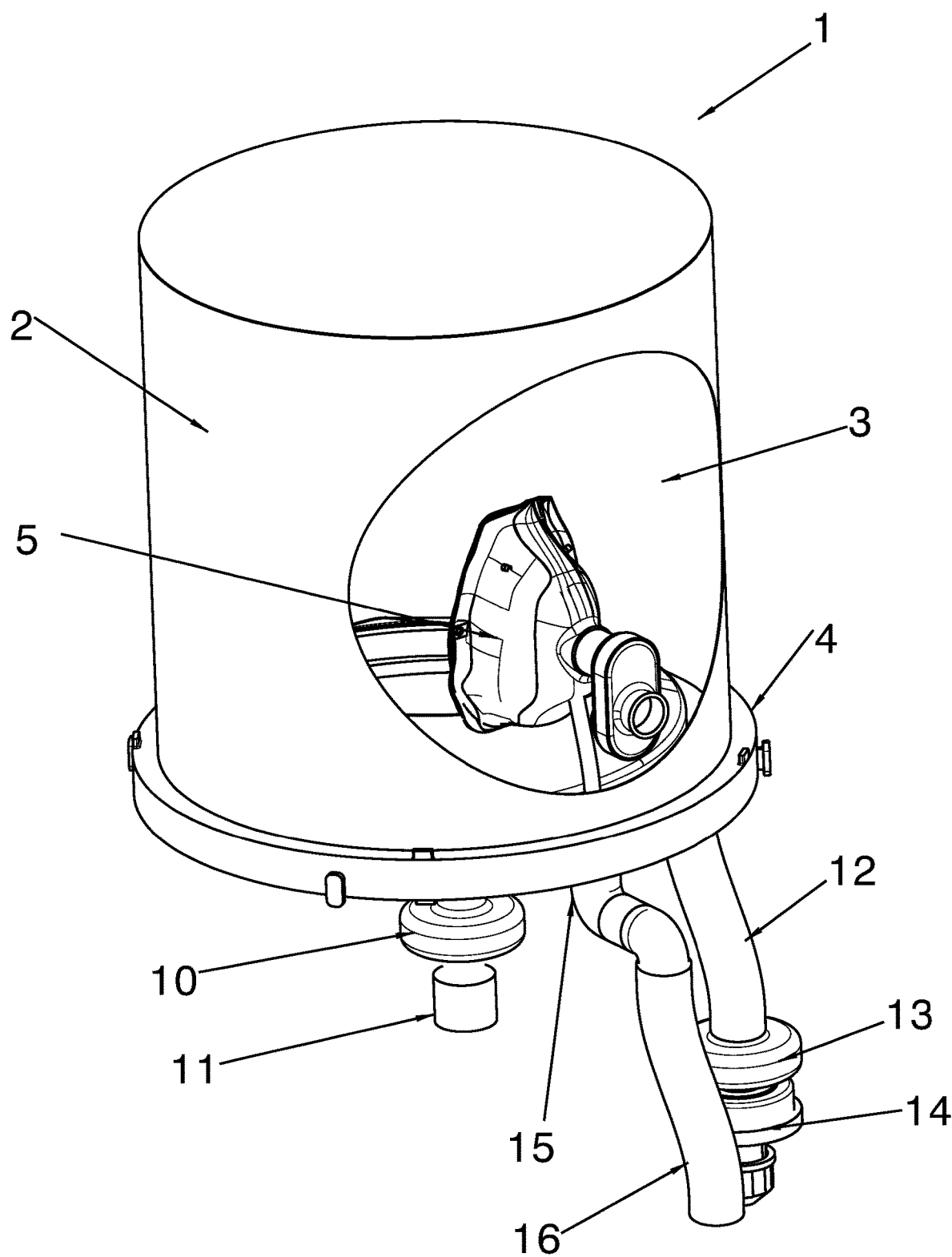
FIG. 3 is a drawing showing the details of the non-invasive ventilation device.

With reference to FIG. 3 a detailed view of the non-invasive ventilation device, 1, is shown. The components are as follows: the hood, 2, the transparent view port, 3, the outer neck ring, 4, the face mask, 5, the viral filter, 10, located in front of the safety pressure relief valve, 11, the exhalation exhaust duct, 12, the viral filter, 13, located before the PEEP valve, 14, the anti-asphyxiation valve, 15, located in the oxygen supply line, 16, that is connected to the hospital in room oxygen supply.

Figure 4:
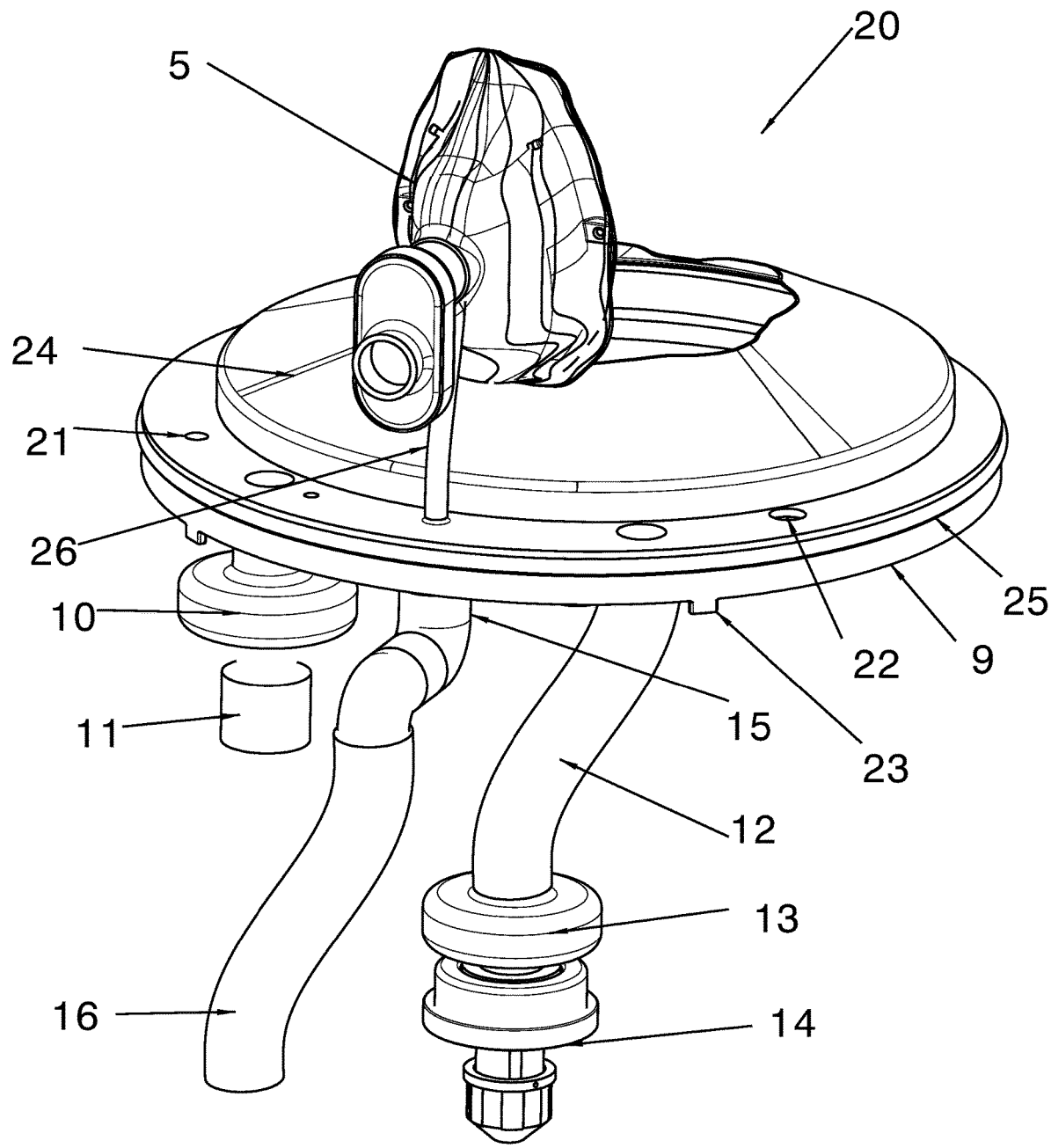
FIG. 4 is a drawing showing the non-invasive ventilation device lower portion (hood removed).

With reference to FIG. 4 a detailed view of the lower part of the non-invasive ventilation device, 20, is shown. The components are as follows: the inner neck ring, 9, the face mask, 5, the viral filter, 10, located in front of the safety pressure relief valve, 11, the exhalation exhaust duct, 12, the viral filter, 13, located before the PEEP valve, 14, the anti-asphyxiation valve, 15, located in the oxygen supply line, 16, that is connected to the hospital in room oxygen supply, and the neck collar, 24, that is an opening custom cut to fit the patient's neck size. Also shown are the locking cams (4 in total located around the inner neck ring, 9), 23, that are used to lock the hood, 2, to the inner neck ring, 9. The internal oxygen line, 26, connects the mask, 5, to the oxygen line, 16. The injected "flow through" elastomer (O-Ring replacement), 25, is also shown. The feeding tube port, 21, and the entertainment port, 22, are shown passing through the inner neck ring, 9.

Figure 5:
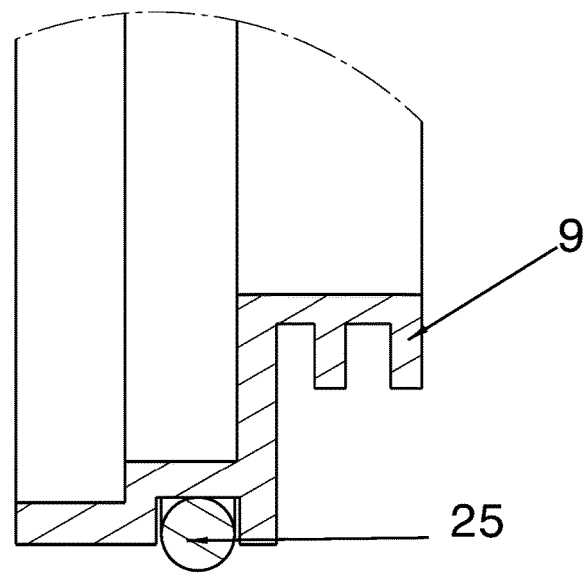
FIG. 5 is a drawing showing the neck ring of the non-invasive ventilation device along with a cross section view thru the neck ring.
Figure 5:
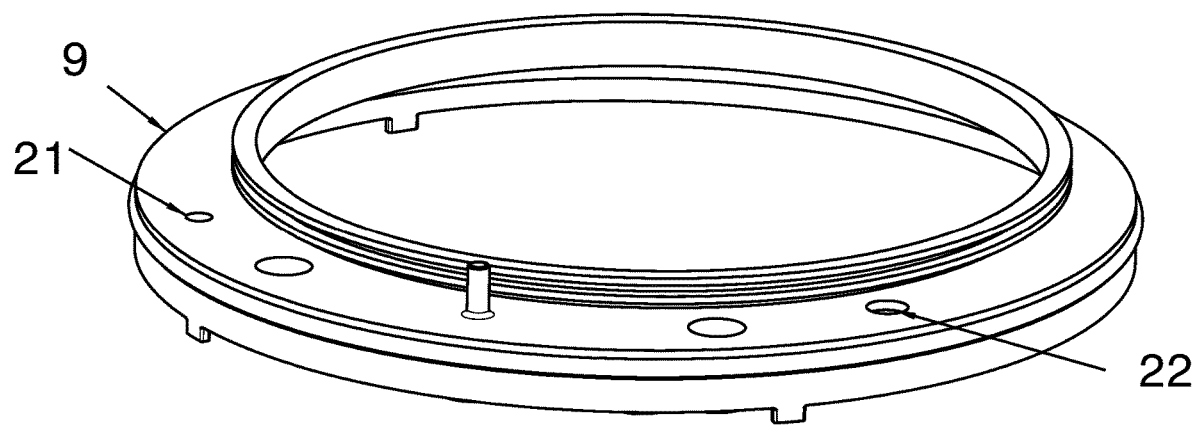

With reference to FIG. 5 a detailed view of the inner neck ring, 9, of the non-invasive ventilation device, 1, is shown. The feeding tube port, 21, and the entertainment port, 22, are shown passing through the inner neck ring, 9. There is also a C/S view of the inner neck ring, 9, shown in this figure. The O-Ring, 25, is also shown mounted on the inner neck ring, 9.

Figure 6:
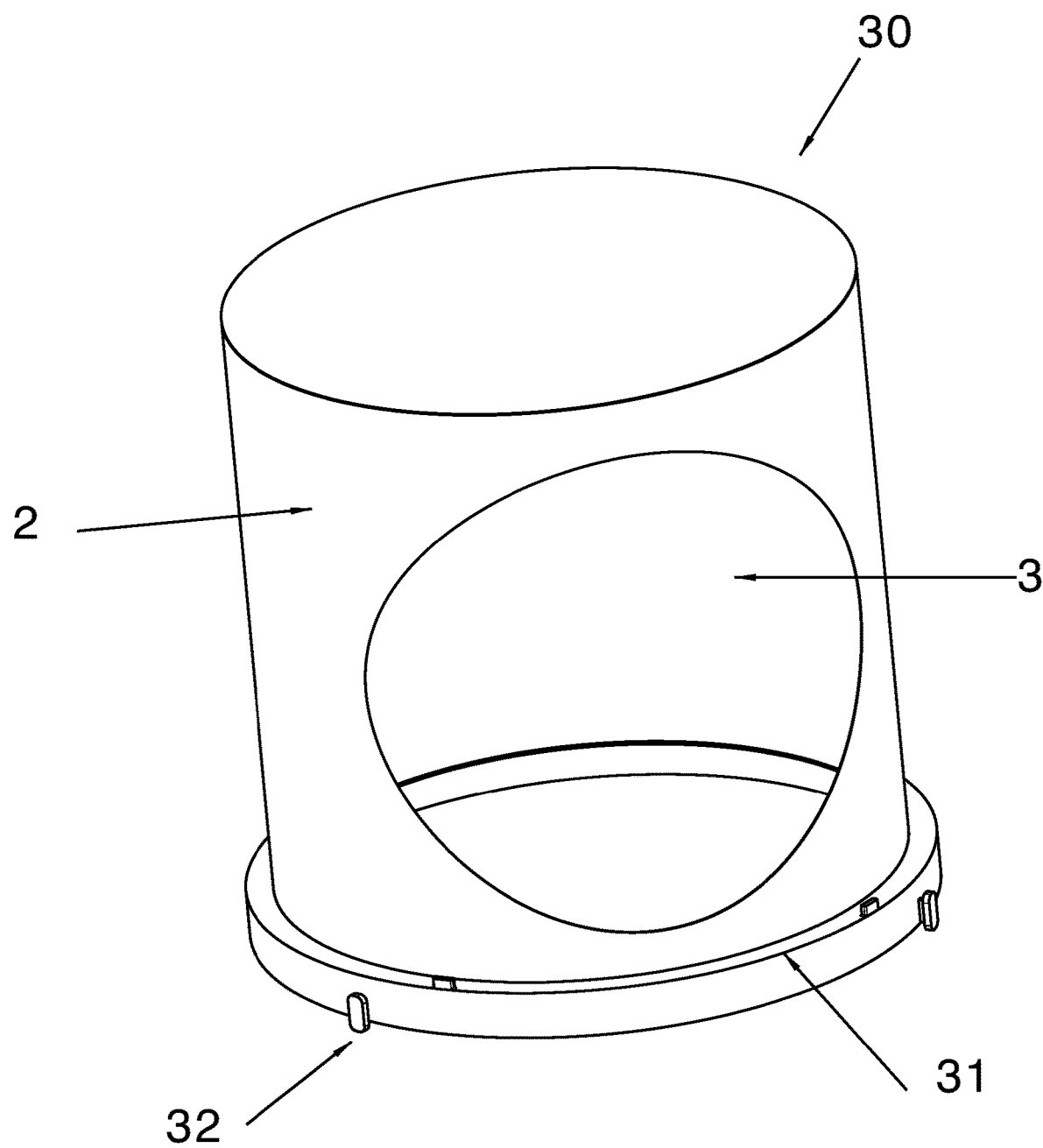
FIG. 6 is a drawing showing the hood of the non-invasive ventilation device.

With reference to FIG. 6 a detailed view of the hood assembly, 30, of the non-invasive ventilation device, 1, is shown. The components shown are the hood, 2, the transparent view port, 3, the hood mounting ring, 31, and the 4 locking clamps which are molded as integral (in-mold assembled) to either or both the hood sealed ring 31 or the, 32. These locking pins, 32, are engaged by the locking cams, 23, shown in FIG. 4 when the hood assembly, 30, is locked into place on the neck ring, 4. Locking the hood assembly, 30, into place on the neck ring, 4, compresses the rubber O-Ring, 25, sealing the non-invasive ventilation device, 1, against oxygen leakage. The locking pins, 32, are also be used to attach retainer straps (that are not shown) that hold the non-invasive ventilation device, 1, to the patient.

Figure 7:
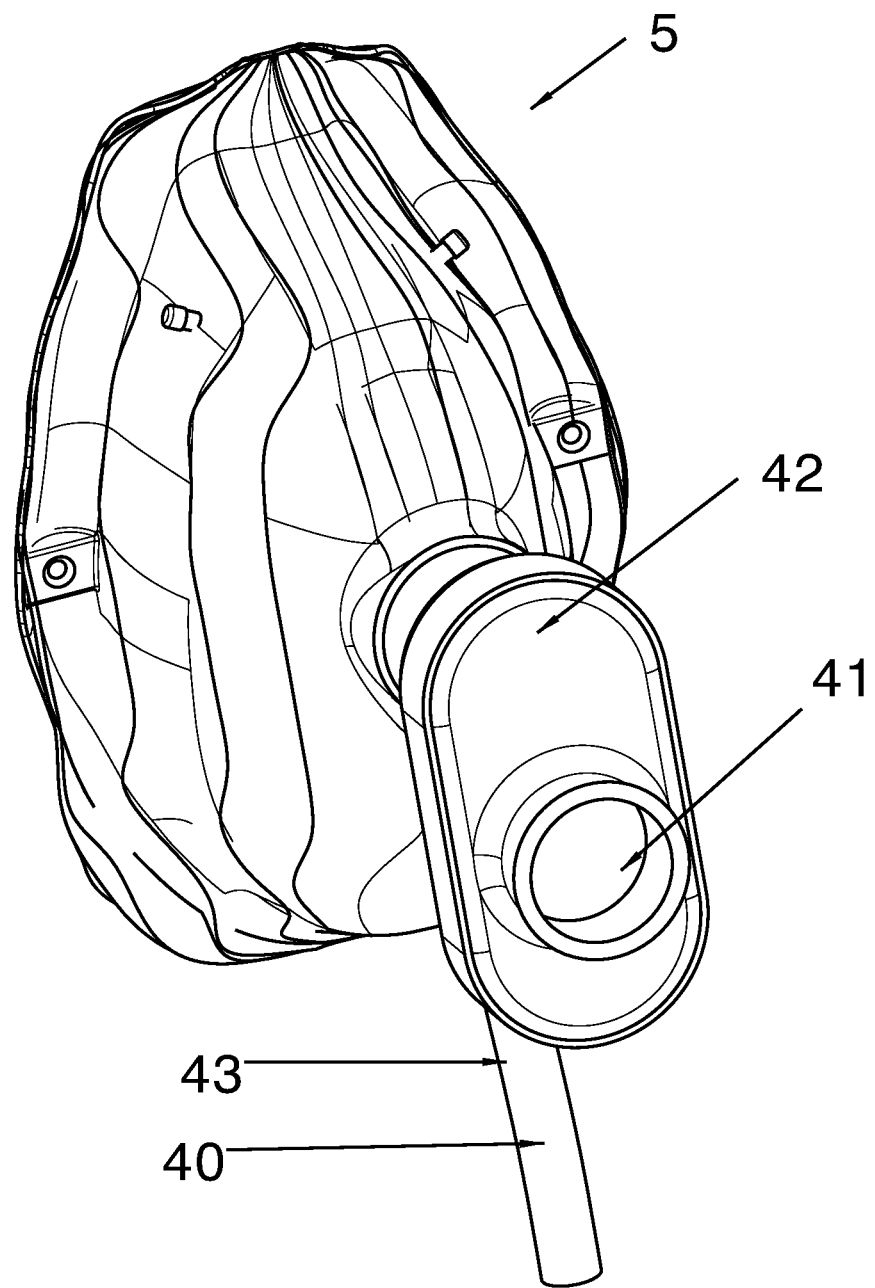
FIG. 7 is a drawing showing a detailed view of the face mask.

With reference to FIG. 7 a detailed view of the face mask, 5, is shown. The components shown are the oxygen or air/oxygen blend input tube, 40, the back flow valve, 43, located in the oxygen or air/oxygen blend input tube, 40, the exhaust port, 41, and the back-flow valve, 42, located before the exhaust port, 41. The back flow valves, 42 and 43, are important in preventing the build-up of condensation in the non-invasive ventilation device, 1.

Figure 8:
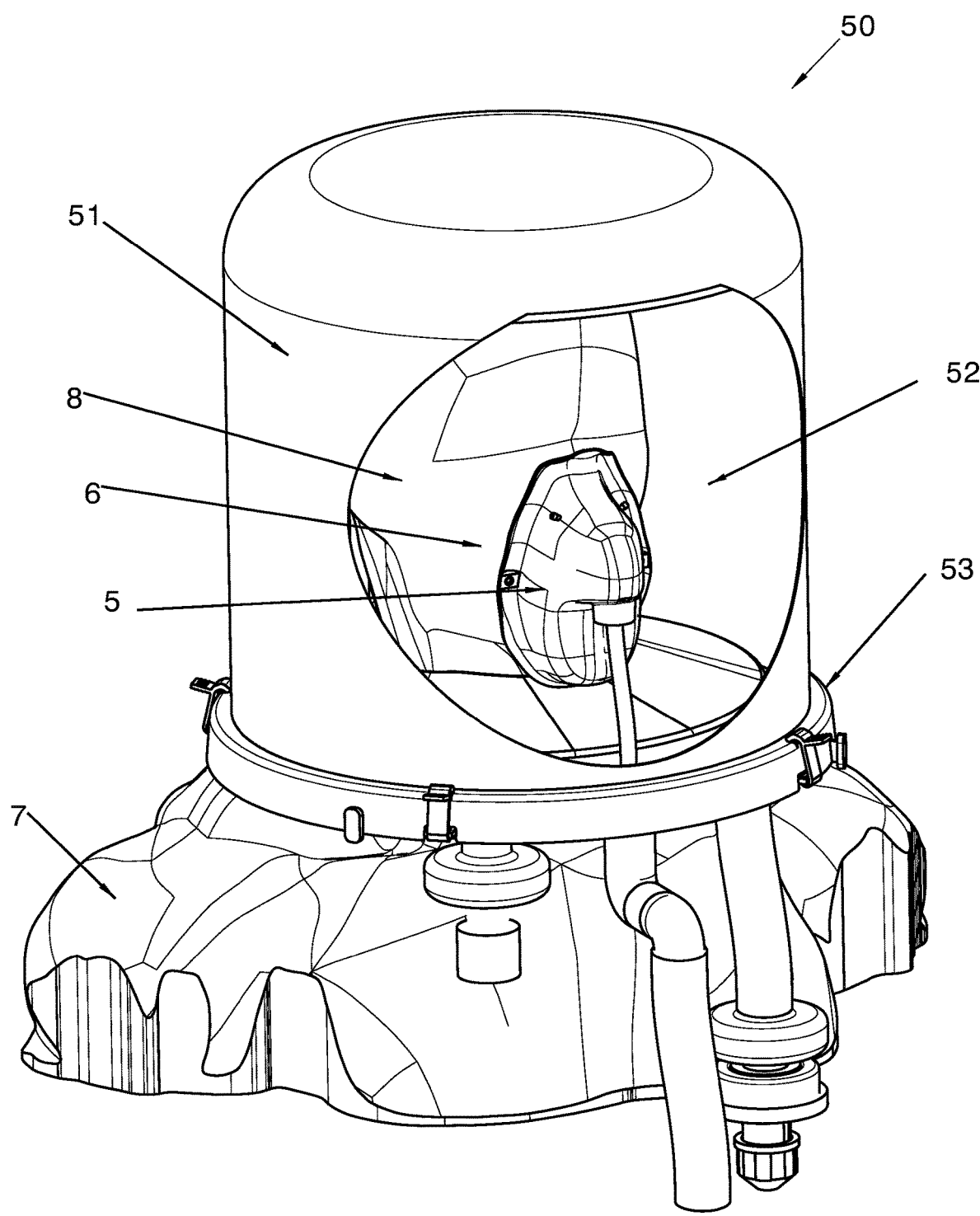
FIG. 8 is a drawing showing a second version the non-invasive ventilation device being worn by a patient.

With reference to FIG. 8 a second version of the non-invasive ventilation device, 50, is shown. The major component pieces are: the hood, 51, the transparent view port, 52, the outer neck ring, 53, the face mask, 5, the patient's head, 6, the patient, 7, and the patient's face, 8. When installing the non-invasive ventilation device, 50, on the patient, 7, the inner neck ring assembly (see FIG. 11), 65, is first lowered over the patient's head, 6, then the face mask, 5, is placed on the patient's face, 8, (making certain that the oxygen or air/oxygen mixture is turned on) and then the hood assembly, 55, is placed over the patient's head, 6, and locked into place.

Figure 9:
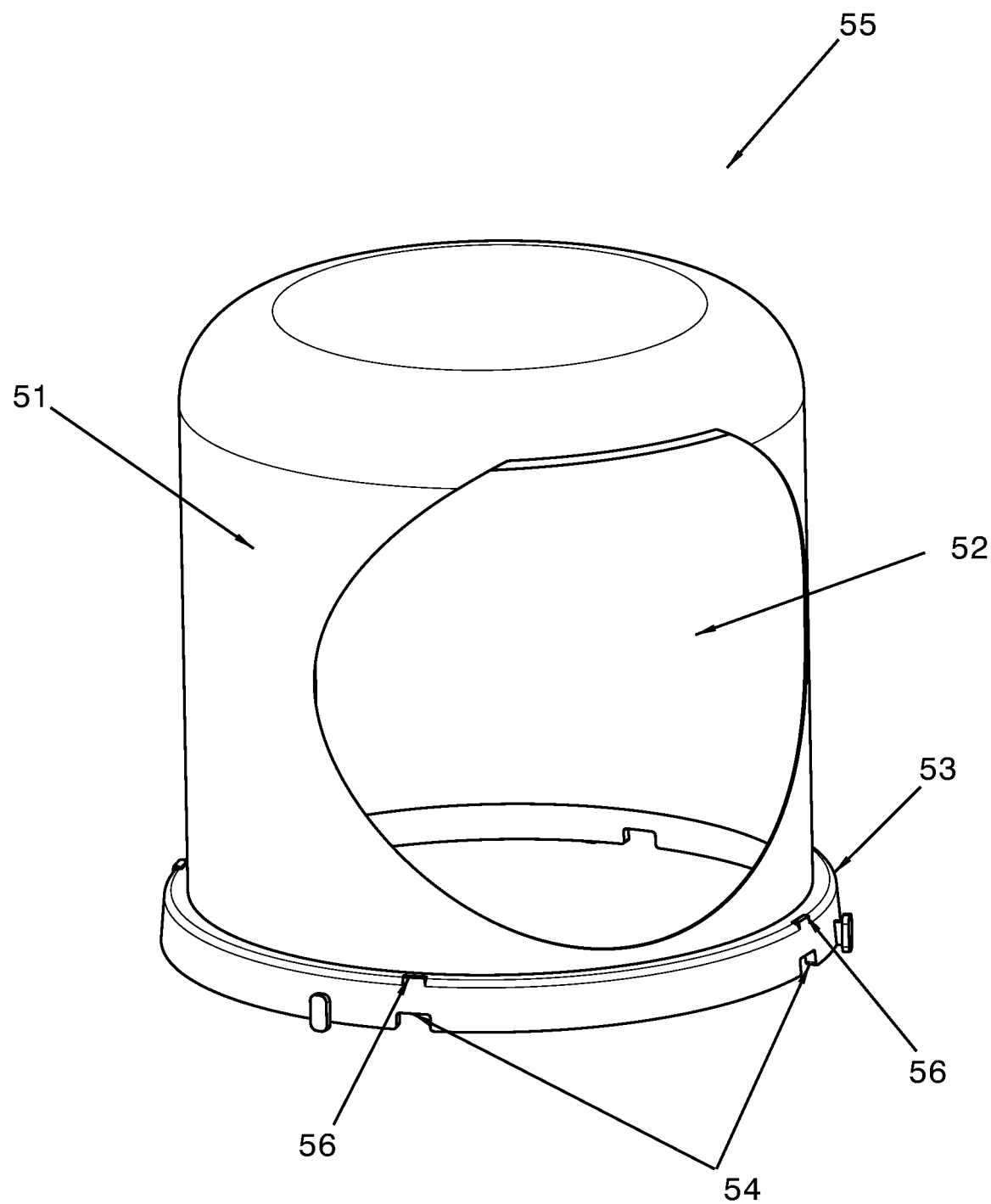
FIG. 9 is a drawing showing the hood and the outer neck ring assembly.

With reference to FIG. 9, the hood assembly, 55, is shown. The hood assembly, 55, consists of three components; the flexible hood, 51, which can be made from transparent elastomers such as Santoprene, Surlyn, TPO (a combination of polymer and filler blends), TPE (thermoplastic elastomers), etc. the transparent widow, 52, and the outer neck ring, 53, which can be made from a rigid plastic such as Polypropylene, ABS, Nylon, etc. the outer neck ring, 53, has 4 notches, 54, to provide clearance for the locking mechanisms, and 4 protrusions, 56, that are used with the locking mechanism.

Figure 10:
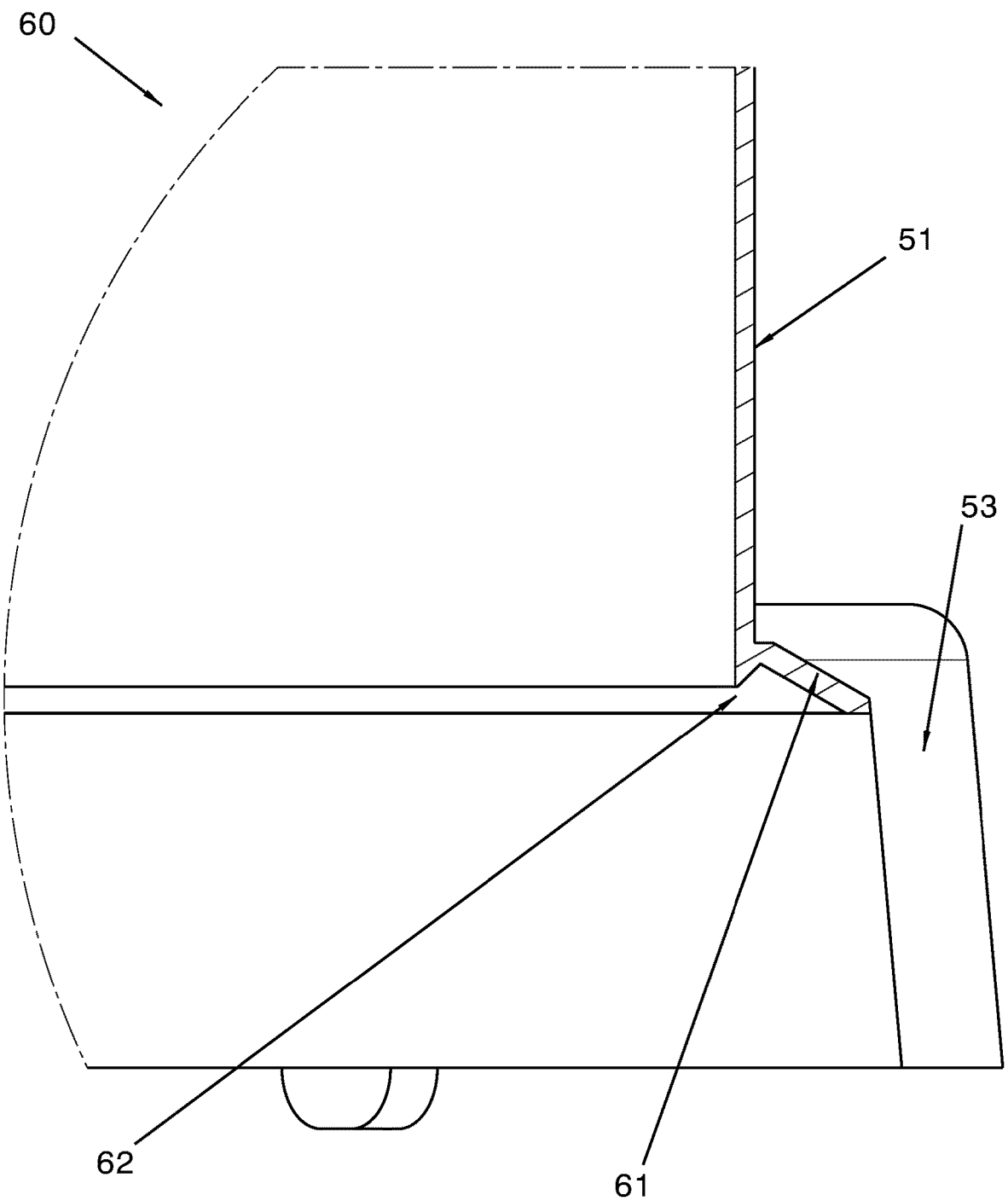
FIG. 10 is a drawing showing the details (in a cross section view) of the outer ring attachment to the hood.

With reference to FIG. 10, a cross section view, 60, through the hood assembly, 55, of FIG. 9 is shown. In this cross section view, 60, the connection between the hood, 51, and the outer neck ring, 53, is shown. The connection area, 61, between the hood, 51, and the outer neck ring, 53, is created using over-molding of the hood, 51, onto the outer neck ring, 53, in a 2-shot rotary mold. A particular feature of the hood, 51, is a molded in inner shield, 62, which is used to provide a pressure activated seal against the inner neck ring, 66, (see FIG. 13). The pressure to activate the inner shield, 62, comes from normal operation of the non-invasive ventilation device, 50.

Figure 11:
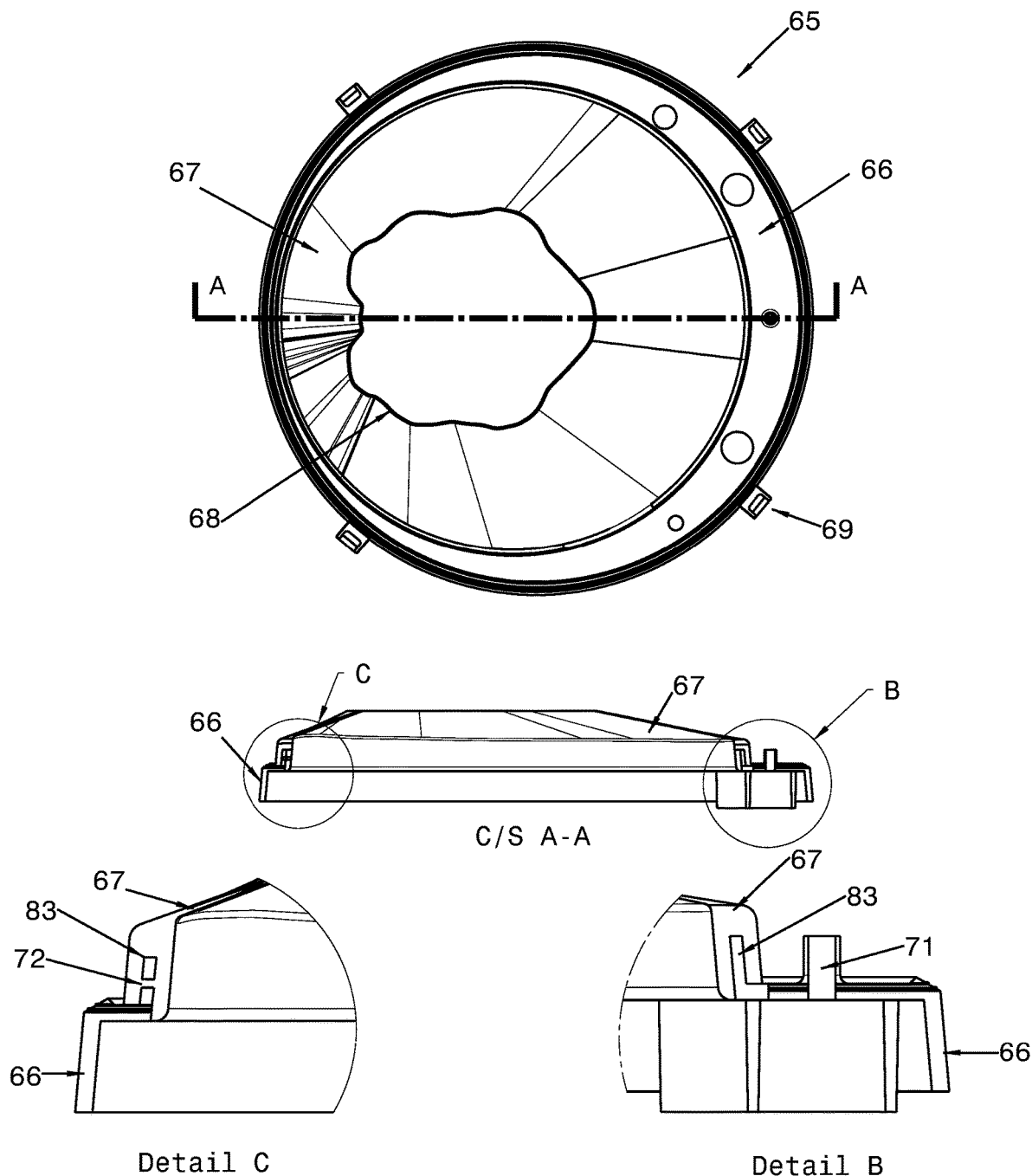
FIG. 11 is a drawing showing the inner neck ring with the over-molded neck collar.

With reference to FIG. 11 the assembly, 65, of the inner neck ring, 66, and the neck collar, 67, is shown. The opening, 68, is cut to a size that is dependent on the size of the patient's neck. A cross section view A-A shows how the inner neck ring, 66, and the neck collar, 67, are connected, the neck collar, 67, is over-molded onto the inner neck ring, 66, in a 2-shot molding process. The neck collar, 67, can be made from transparent elastomers such as Santoprene, Surlyn, TPO (a combination of polymer and filler blends), TPE (thermoplastic elastomers), etc., while the inner neck ring, 66, can be made from a rigid plastic such as Polypropylene, ABS, Nylon, etc. Detail B shows the over-molding of the neck collar, 67, onto the inner neck ring, 66, in this area the vertical rib, 83, is solid. Also shown in detail B is the oxygen/oxygen air mixture inlet, 71. Detail C shows the over-molding of the neck collar, 67, onto the inner neck ring, 66, in this area the vertical rib, 83, has a slot, 72, through it that provides a connection for the plastic material of the neck ring, 67, to connect on both sides of the vertical rib, 83, providing a strong mechanical connection between the neck collar, 67, and the inner neck ring, 66.

Figure 12:
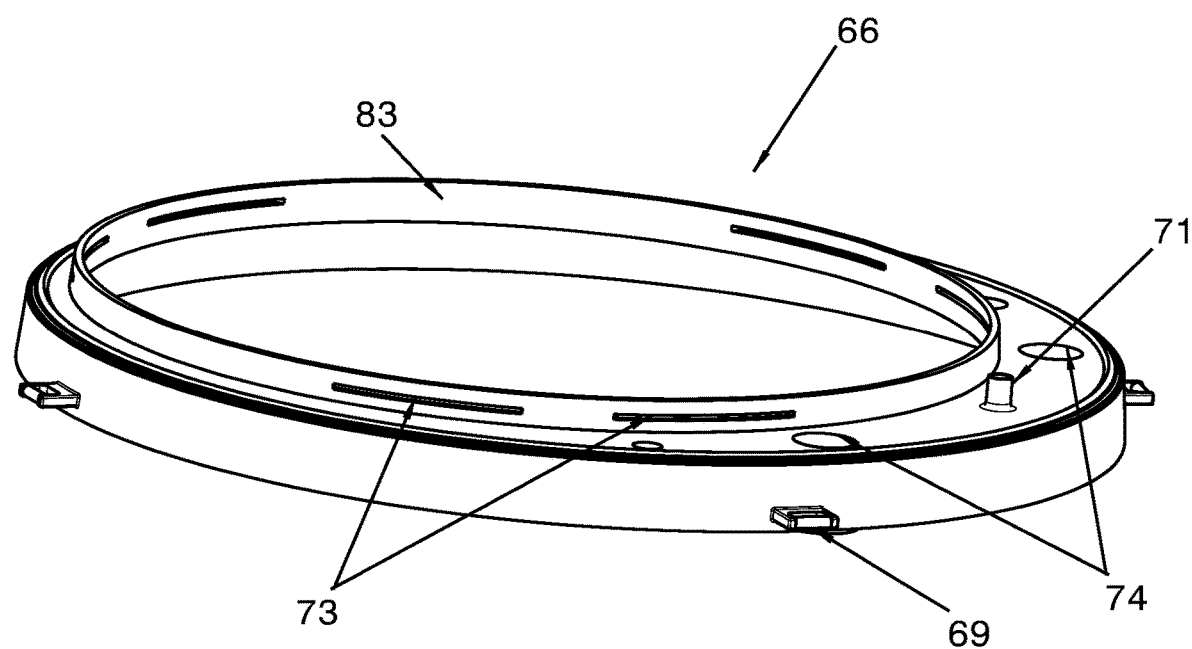
FIG. 12 is a drawing showing the details of the inner neck ring.

With reference to FIG. 12 the inner neck ring, 66, is shown. Particular features that are incorporated into the inner neck ring, 66, are: the oxygen/oxygen air mixture inlet, 71, the accessory ports, 74, the vertical rib, 83, with slots, 73, through it, which provide a channel for the plastic material of the neck ring, 67, to connect on both sides of the vertical rib, 83, and the hinge points, 69.

Figure 13:
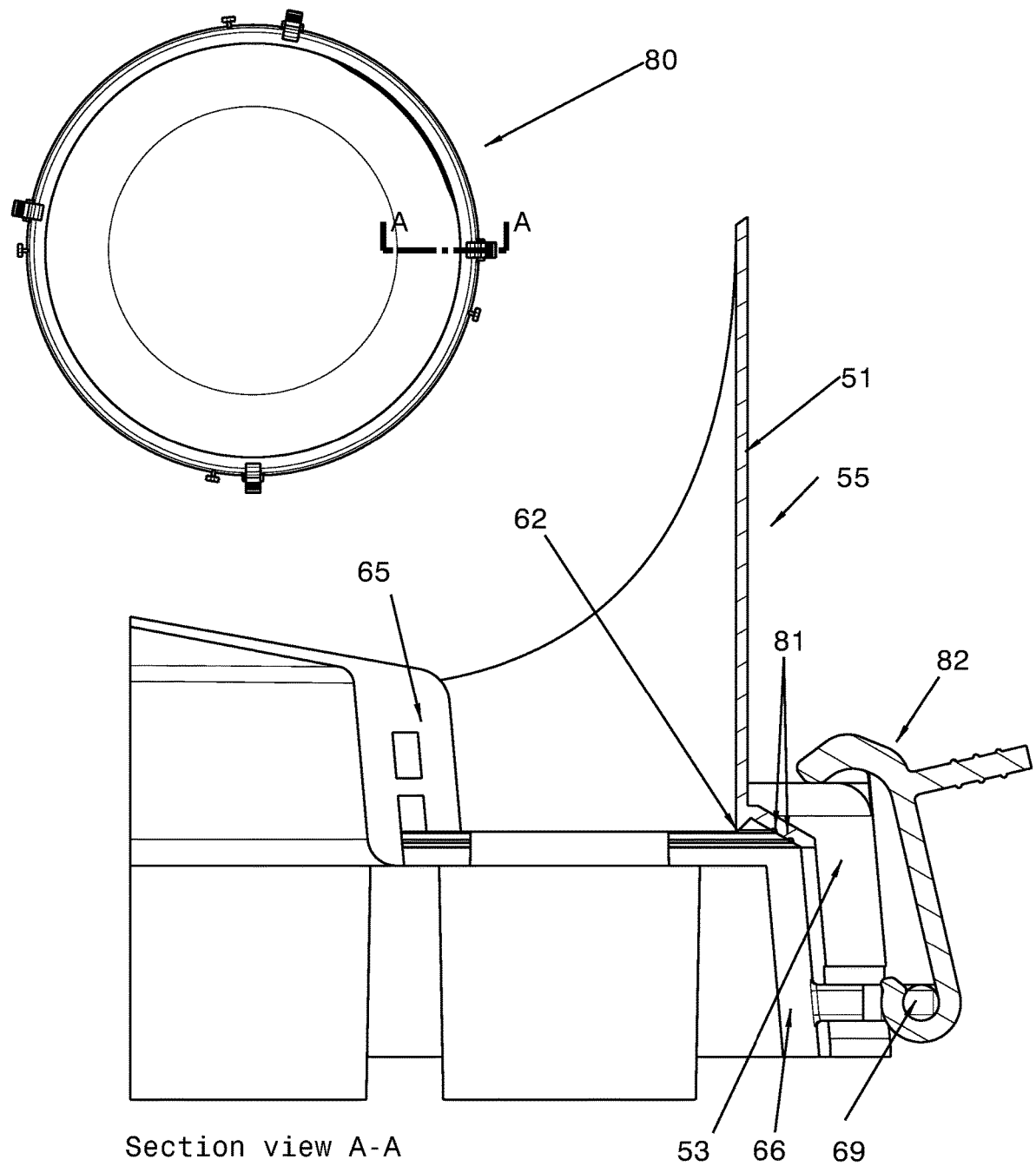
FIG. 13 is a drawing showing a detailed view of the clamping mechanism.

With reference to FIG. 13 the inter connection, 80, of the hood assembly, 55, and the inner neck ring assembly, 65, is shown. The inter connection, 80, between the hood assembly, 55, and the inner neck ring assembly, 65, is accomplished by engaging the 4 clamps, 82, that rotate about the hinges, 69, mounted on the inner neck ring, 66. The 4 clamps, 82, are rotated to engage the top of the outer neck ring, 53, pulling it towards the inner neck ring assembly, 65, this action forces two seals to be made, the first is the contact between the inner shield, 61, and the top of the inner neck ring, 66, while the second is the contact between the hood, 51, and the inner neck ring, 66, which is enhanced by the action of the two sharp ribs, 81, that are pressed into the flexible material of the hood, 51.

This invention has been described with reference to detailed descriptions of preferred embodiments. The details of the descriptions are given for the sake of explanation only and are not intended as limitations upon the scope and spirit of the appended claims.

What is claimed is:

1. A non-invasive ventilation device that includes the following components:
    a) a hood with an outer neck ring that is in-mold assembled using over-molding technology;
    b) an inner neck ring that is in-mold assembled using over-molding technology to create a neck collar;
    c) manually operated clips to pull the two rings together, creating an air tight seal; and
    d) sharp ribs on the surface of the inner neck ring, located in the engagement area with the hood material such that engaging the manually operated clips forces the sharp ribs into the hood material to create a very effective air tight seal;
    wherein the non-invasive ventilation device is used to provide a patient with an oxygen or air/oxygen blend atmosphere for pressurized breathing assistance.

2. The non-invasive ventilation device according to claim 1 wherein the hood material has a flexible lip at its bottom, providing an additional seal due to the pressure of the oxygen or air/oxygen mixture inside the hood.

3. The non-invasive ventilation device according to claim 1 wherein the hood is over-molded from a clear flexible plastic, while the outer neck ring is molded from a rigid plastic.

4. The non-invasive ventilation device according to claim 3 wherein the hood is over-molded from a clear flexible plastic, while the outer neck ring is molded from a rigid plastic in a two shot molding process.

5. The non-invasive ventilation device according to claim 1 wherein the neck collar is over-molded from a flexible plastic, while the inner neck ring is molded from a rigid plastic.

6. The non-invasive ventilation device according to claim 1 wherein the neck collar is over-molded from a flexible plastic, while the inner neck ring is molded from a rigid plastic in a two shot molding process.

7. The non-invasive ventilation device according to claim 1 wherein the neck collar is over-molded from a flexible plastic, while the inner neck ring is molded from a rigid plastic that has holes or slots in it to allow the over-molded neck collar plastic to form a mechanical bond by flowing through the holes or slots before hardening.

* * * * *